United States Patent [19]
Parker et al.

[11] 3,931,173
[45] Jan. 6, 1976

[54] DIOXOCIN CARBOXAMIDE DERIVATIVES
[75] Inventors: Roger Alan Parker, Cincinnati, Ohio; David Lawrence Wenstrup, Edgewood, Ky.
[73] Assignee: Richardson-Merrell Inc., Wilton, Conn.
[22] Filed: July 22, 1971
[21] Appl. No.: 165,357

[52] U.S. Cl. 260/247.7 T; 260/268 TR; 260/293.58; 260/295 T; 260/295.5 T; 260/326.5 CA; 260/340.3; 424/248
[51] Int. Cl.² .................................. C07D 295/18
[58] Field of Search.... 260/247.7 F, 340.3, 247.7 T, 260/293.58, 326.5 CA, 295 T, 295.5 T

[56] References Cited
UNITED STATES PATENTS

| | | | |
|---|---|---|---|
| 3,551,484 | 12/1970 | Lewis et al. | 260/558 D |
| 3,553,234 | 1/1971 | Johnson et al. | 260/340.3 |
| 3,652,646 | 3/1972 | Leigh et al. | 260/247.2 A |
| 3,652,670 | 3/1972 | Horrom et al. | 260/558 D |

Primary Examiner—Nicholas S. Rizzo
Assistant Examiner—Jose Tovar
Attorney, Agent, or Firm—George W. Rauchfuss, Jr.; Eugene O. Retter

[57] ABSTRACT
Novel dioxocin carboxamide derivatives, which reduce blood lipids in warm blooded animals and are useful in the treatment of hyperlipidemic states, are represented by compounds of the following formula:

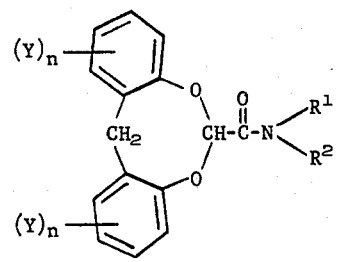

Formula I wherein each Y is selected from the group consisting of hydrogen, halogen such as chlorine, bromine, fluorine or iodine, or lower alkyl of from 1 to 4 carbon atoms; n is an integer of from 1 to 3; $R^1$ and $R^2$ may be the same or different, and each is selected from the group consisting of hydrogen, lower alkyl of from 1 to 4 carbon atoms, benzyl, picolyl, cycloalkyl of from 3 to 6 carbon atoms, phenyl, or substituted phenyl in which case the substituents on the substituted phenyl are selected from lower alkyl of from 1 to 4 carbon atoms; or $NR^1R^2$ taken together represent a saturated monocyclic heterocyclic group such as, pyrrolidino, piperidino, morpholino, piperazino or N-(lower alkyl)-piperazino, and pharmaceutically acceptable salts of the salt forming compounds.

9 Claims, No Drawings

DIOXOCIN CARBOXAMIDE DERIVATIVES

FIELD OF INVENTION

This invention relates to novel dioxocin carboxamide derivatives. More particularly this invention relates to dibenzo [d,g] [1,3]dioxocin-6-carboxamide derivatives and pharmaceutically acceptable acid addition salts of the appropriate compounds, which reduce blood lipids in warm blooded animals and are useful in the treatment of hyperlipidemic states.

BACKGROUND OF THE INVENTION

Cardiovascular diseases have been the leading cause of death in the United States in recent years. Mortality statistics show that of the various cardiovascular diseases, atherosclerotic process occurring in the coronary or cerebral vessels are responsible for a large majority of deaths. A strong correlation exists between elevated plasma cholesterol and triglyceride levels and the development of atherosclerotic disease. Accordingly, it is considered desirable to reduce plasma cholesterol and triglyceride levels toward normal in treating diseases characterized by elevated blood lipid levels, e.g., coronary heart disease and stroke.

SUMMARY OF INVENTION

The novel compounds of this invention are represented by those having the following formula:

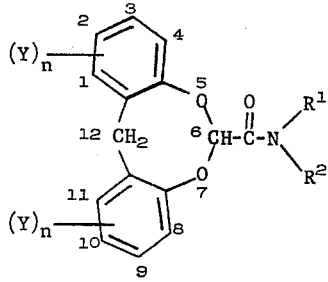

Formula I wherein each Y is selected from the group consisting of hydrogen, halogen such as chlorine, fluorine, bromine or iodine, or lower alkyl of from 1 to 4 carbon atoms; n is an integer of from 1 to 3; $R^1$ and $R^2$ may be the same or different, and each is selected from the group consisting of hydrogen, lower alkyl of from 1 to 4 carbon atoms, benzyl, picolyl; cycloalkyl of from 3 to 6 carbon atoms, phenyl or substituted phenyl in which case the substituents on the substituted phenyl are selected from lower alkyl of from 1 to 4 carbon atoms; or $NR^1R^2$ taken together represent a saturated monocyclic heterocyclic group such as, pyrrolidino, piperidino, morpholino, piperazino or N-(lower-alkyl)piperazino. Also included within the scope of this invention are the pharmaceutically acceptable acid addition salts of these compounds where applicable.

DETAILED DESCRIPTION OF INVENTION

Preferred compounds of this invention are represented by the following Formula II:

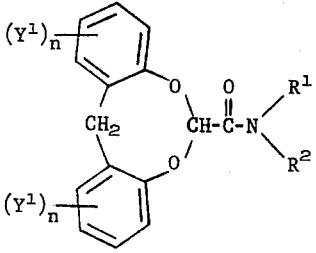

Formula II wherein each $Y^1$ represents a halogen atom, such as, chlorine, fluorine, bromine or iodine, and n and

have the meanings given hereinbefore.

The most preferred compounds of this invention are represented by the following Formula III;

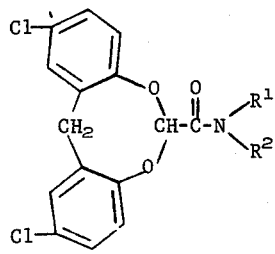

Formula III wherein —$NR^1R^2$ has the meaning defined hereinbefore.

As examples of the lower alkyl radicals that $R^1$ and $R^2$ may represent as well as the lower alkyl radicals which may be present as substituents on the substituted phenyl radicals that the symbols $R^1$ and $R^2$ may represent in the above Formulas I, II and III there may be mentioned, for example, methyl, ethyl, propyl, isopropyl, butyl and the like.

As examples of the cycloalkyl radicals which the symbols $R^1$ and $R^2$ may represent in the above Formula I there may be mentioned cyclopropyl, cyclobutyl, cyclopentyl and cyclohexyl.

As examples of compounds of this invention there may be mentioned, for example, 2,10-dichloro-12H-dibenzo[d,g][1,3]dioxocin-6-carboxamide,
1,11-dipropyl-N-cyclohexyl-12H-dibenzo[d,g][1,3-]dioxocin-6-carboxamide,
N,N-dibutyl-12H-dibenzo[d,g][1,3]dioxocin-6-carboxamide,
2,10-dichloro-N-ethyl-12H-dibenzo[d,g][1,3]dioxocin-6-carboxamide,
2,10-dichloro-N(o-tolyl)-12H-dibenzo[d,g][1,3]dioxocin-6-carboxamide, 4-(2,10-dichloro-12H-dibenzo[d,g][1,3]dioxocin-6-carbonyl)morpholine,
N-cyclohexyl-3,9-dichloro-12H-dibenzo[d,g][1,3-]dioxocin-6-carboxamide,
N-(p-tolyl)-12H-dibenzo[d,g][1,3]dioxocin-6-carboxamide,
N-benzyl-2,10-dimethyl-12H-dibenzo[d,g][1,3]dioxocin-6-carboxamide,
1-(2,10-dichloro-12H-dibenzo[d,g][1,3]dioxocin-6-carbonyl)-4-methylpiperazine,
1-(2,10-diethyl-12H-dibenzo[d,g][1,3]dioxocin-6-carbonyl)piperazine, and the like.

Pharmaceutically acceptable acid addition salts of the base compounds of this invention are those of any suitable inorganic or organic acids. Suitable inorganic acids are, for example, hydrochloric, hydrobromic, sulfuric or phophoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, Salicyclic, 2-phenoxybenzoic and the like, or sulfonic acids such as methane sulfonic, 2-hydroxyethane sulfonic acid and the like.

The novel compounds of this invention reduce blood lipids, particularly lipoproteins containing cholesterol and triglycerides in warm-blooded animals and are useful in the treatment of hyperlipidemic states such as are encountered in patients with cardiovascular diseases, especially atherosclerotic diseases that can result in heart failure and stroke. The compounds of this invention can be used in the form of pharmaceutical preparations which contain the novel compound suitable for oral or parenteral administration. The quantity of compound in unit dosage form can vary over a wide range to provide from about 10 mg/kg to about 4 g/kg of body weight and preferably 50 mg/kg to 1 g/kg of body weight of the subject per day to achieve the desired effect.

To illustrate the utility of the compounds of this invention young male rats of the Wistar strain weighing initially about 170 grams were given free access to a diet to which the test compound was added. This diet was prepared by pouring an ethanolic solution of the compound over commercial PURINA CHOW[1] and mixing thoroughly allowing the solvent to evaporate. Groups of animals were given these diets for a period of 11 days. A control group was given the same diet to which no active compound was added. At the end of the treatment period, all rats were bled by cardiac puncture and the plasma was analyzed for cholesterol and triglyceride content on a Technicon AUTOANALYZER[2]. The results are given in the following Table I wherein the Example Nos. correspond to the specific Examples which illustrate the invention.

[1] Trademark of Ralston Purina Company, St. Louis, Missouri.
[2] Trademark of Technicon Corporation, Tarryton, New York 10591.

Table I

| Example No. | Daily Dose mg/kg (a) | No. Rats | Plasma Cholesterol % Reduction* | Plasma Triglycerides % Reduction* |
|---|---|---|---|---|
| 1 | 30.0 | 6 | 22$^x$ | 57$^x$ |
| 2 | 28.0 | 6 | 37$^x$ | 67$^x$ |
|   | 9.9 | 5 | 6 | 55$^x$ |
|   | 3.0 | 6 | 0 | 34$^x$ |
| 3 | 30.0 | 6 | 24$^y$ | 71$^x$ |
| 4 | 31.0 | 6 | 23$^x$ | 75$^x$ |
| 5 | 31.0 | 6 | 10 | 72$^x$ |
| 6 | 30.0 | 6 | 22$^x$ | 44$^z$ |
| 7 | 30.0 | 6 | 26$^y$ | 66$^z$ |
| 8 | 28.0 | 6 | 25$^x$ | 78$^y$ |

(a) Determined by measuring food consumption.
*P values: x = <0.01; y = <0.05; z = 0.1; ∈ = >0.1 (not significant).

The compounds of this invention are prepared by the reaction of a compound of the formula

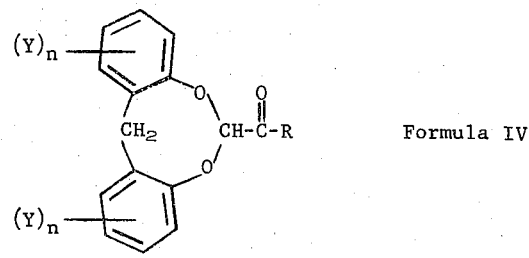

Formula IV with an amine of the following formula

Formula V wherein the various symbols Y, n, R$^1$ and R$^2$ have the meanings defined hereinbefore and R represents halogen, such as chlorine or bromine, or lower alkoxy of from 1 to 4 carbon atoms.

The compounds of Formula IV are parepared by reaction of salts of an appropriately substituted 2,2'-methylenebisphenol with a dihaloacetic acid, as generally described in U.S. Pat. No. 3,553,234 issued Jan. 5, 1971, to give a 12H-dibenzo[d,g][1,3]dioxocin-6-carboxylic acid derivative, which is subsequently treated with thionyl halide, for example, thionyl chloride to give the corresponding acid halide, or is esterified by generally known procedures to give the corresponding ester derivative. The acid halide may be used as the unpurified reaction product or may be purified by recrystallization.

Of typical amines as represented by Formula V there can be mentioned for example; ammonia; primary amines such as ethylamine, propylamine, aniline, β-picolylamine and the like; and secondary amines such as dimethylamine, dipropylamine, piperidine, morpholine, pyrrolidine, piperazine, N-methylpiperazine and the like.

The above general reaction may be carried out with or without solvent and/or base. The temperature of the reaction may vary from 0°C to the boiling point of the solvent employed. When R in the above Formula IV represent a halogen atom it is preferred that the reaction be carried out at room temperature, and when R represents lower alkoxy it is preferred that the reaction be carried out at the reflux temperature of the solvent employed. The reaction time may vary from 2 to 24 hours, but preferably the reaction is completed in from 2 to 16 hours.

Typical solvents which may be used in the above general reaction include aromatic hydrocarbons such as benzene, toluene and the like, pyridine, triethylamine and the like or the reactant amine represented by Formula V.

A variety of bases may be employed in the above general reaction. For example, when R in the above Formula IV represents a halogen atom, typical bases which may be used include triethylamine, pyridine and the like; potassium hydroxide, sodium hydroxide, or the reactant amine as represented by Formula V. When R in the above Formula IV is lower alkoxy a base such as triethylamine pyridine and the like may find use in the reaction. The following specific examples illustrate the invention.

EXAMPLE 1

2,10-Dichloro-N-(3-pyridylmethyl)-12H-dibenzo[d,g][1,3]dioxocin-6-carboxamide

To 15 g of 2,10-dichloro-12H-dibenzo[d,g][1,3]dioxocin-6-carboxylic acid was added 75 ml of thionyl chloride, and the heterogenous mixture was refluxed with occasional stirring until it became homogenous. The mixture was refluxed for an additional 2 hours after which the thionyl chloride was distilled off under reduced pressure affording a solid residue which was dissolved in 300 ml of dry benzene by warming on a steam bath. The benzene was distilled off under reduced pressure affording a white crystalline residue to which was added 500 ml of dry benzene. The mixture was stirred at room temperature until homogenous then 35 g of 3-aminomethylpyridine was added. After standing at room temperature for 2 hours the mixture was heated to reflux for an additional 3 hours, cooled to room temperature, poured into ice water and separated. Methanol was added to aid the solubility of the product in the organic layer. The organic layer was washed with water and distilled under reduced pressure resulting in a residue which was dried and recrystallized twice from methanol-acetone (1:1) to give the desired product, M.P. 225°–226°C.

Similarly by selecting the appropriate starting materials the compounds contained in the following Table II may be prepared.

Table II

| Ex. | Compound | M.P.°C |
|---|---|---|
| 2 | 2,10-dichloro-12H-dibenzo[d,g][1,3]-dioxocin-6-carboxamide | 265–267 |
| 3 | 2,10-dichloro-N-ethyl-12H-dibenzo[d,g]-[1,3]dioxocin-6-carboxamide | 254–257 |
| 4 | 2,10-dichloro-N,N-dimethyl-12H-dibenzo-[d,g][1,3]dioxocin-6-carboxamide | 195–197 |
| 5 | 1-(2,10-dichloro-12H-dibenzo[d,g][1,3]-dioxocin-6-carbonyl)-4-methylpiperazine | 223–225 |
| 6 | 1-(2,10-dichloro-12H-dibenzo[d,g][1,3]-dioxocin-6-carbonyl)piperidine | 212–215 |
| 7 | 4-(2,10-dichloro-12H-dibenzo[d,g][1,3]-dioxocin-6-carbonyl)morpholine | 246–249 |
| 8 | 2,10-dichloro-N(o-tolyl)-12H-dibenzo-[d,g][1,3]dioxocin-6-carboxamide | 210–213 |

EXAMPLE 9

N,N-Diethyl-2,10-dimethyl-12H-dibenzo[d,g][1,3]dioxocin-6-carboxamide

A mixture of 27.4 g (0.120 mole) of 2,2'-methylene bis-p-cresol, 15.5 g (0.120 mole) of dichloroacetic acid, 66.5 g (0.480 mole) of potassium carbonate and 500 ml of isopropyl alcohol was refluxed for 24 hours with vigorous stirring after which 15.5 g. (0.120 mole) of dichloroacetic acid was added and the mixture was refluxed with stirring for 64 hours. The isopropyl alcohol was removed by distillation and replaced with 500 ml of water. The precipitate was collected, washed with 2% aqueous potassium hydroxide, suspended in 1 liter of water, and the suspension was acidified to litmus with 10% aqueous HCl. The resulting precipitate was collected and dried affording 2,10-dimethyl-12H-dibenzo[d,g][1,3]dioxocin-6-carboxylic acid, m.p. 200°–205°C (dec.).

The carboxylic acid was dissolved in 300 ml of methanol and 2 ml of concentrated sulfuric acid was added. The mixture was refluxed for 1 hour, cooled, the resulting crystals collected and recrystallized from methanol-acetone to give methyl 2,10-dimethyl-12H-dibenzo[d,g][1,3]dioxocin-6-carboxylate, m.p. 158°–160°C. The methyl ester and excess diethylamine are refluxed for 16 hours. The remaining diethylamine is removed, and N,N-diethyl-2,10-dimethyl-12H-dibenzo[d,g][1,3]dioxocin-6-carboxamide is obtained.

Following the procedure of Example 1 only substituting for 2,10-dichloro-12H-dibenzo[d,g][1,3]dioxocin-6-carboxylic acid and 3-amino-methylpyridine appropriate amounts of the starting materials listed in Table II the respective products are obtained.

| Example No. | Dioxocin Reactant | Amine Reactant | Final Product |
|---|---|---|---|
| 10 | 12H-dibenzo[d,g][1,3]-dioxocin-6-carboxylic acid | [N,N]dibutyl-amine | N,N-dibutyl-12H-dibenzo[d,g][1,3]-dioxocin-6-carboxamide |
| 11 | 2,4,8,10-tetrachloro-12H-dibenzo[d,g][1,3]-dioxocin-6-carboxylic acid | benzylamine | N-benzyl-2,4,8,10-tetrachloro-12H-dibenzo[d,g][1,3]dioxocin-6-carboxamide |
| 12 | 1,2,4,8,10,11-hexachloro-12H-dibenzo[d,g][1,3]dioxocin-6-carboxylic acid | ammonia | 1,2,4,8,10,11-hexachloro-12H-dibenzo[d,g][1,3]dioxocin-6-carboxamide |
| 13 | 2,10-dichloro-12H-dibenzo[d,g][1,3]-dioxocin-6-carboxylic acid | cyclopentylamine | N-cyclopentyl-2,10-dichloro-12H-dibenzo[d,g][1,3]dioxocin-6-carboxamide |
| 14 | 2,4,8,10-tetramethyl-12H-dibenzo[d,g][1,3]-dioxocin-6-carboxylic acid | pyrrolidine | 1(2,4,8,10-tetramethyl-12H-dibenzo[d,g][1,3]dioxocin]-6-carbonyl)pyrrolidine |

We claim:
1. A compound selected from
A. a compound of the formula

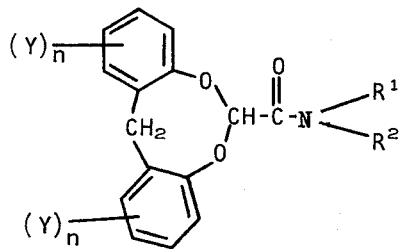

or

B. a pharmaceutically acceptable acid addition salt of the salt forming compounds, wherein each Y is selected from the group consisting of hydrogen, or chlorine; n is 1; $R^1$ and $R^2$ are hydrogen, lower alkyl of from 1 to 4 carbon atoms, picolyl, or o-tolyl or $-NR^1R^2$ taken together are piperidino, or morpholino.

2. A compound of claim 1 wherein one of said chlorine atoms as represented by Y is attached in the 2-position of the dibenzo[d,g][1,3]dioxocin ring and the remaining chlorine atom is attached in the 10-position of the dibenzo[d,g][1,3]dioxocin ring.

3. A compound of claim 2 which is 2,10-dichloro-N-(3-pyridyl-methyl)-12H-dibenzo[d,g][1,3]dioxocin-6-carboxamide or the pharmaceutically acceptable acid addition salts thereof.

4. A compound of claim 2 which is 2,10-dichloro-12-pyridylmethyl)-d,g][1,3]dioxocin-6-carboxamide.

5. A compound of claim 2 which is 2,10-dichloro-N-ethyl-12H-dibenzo[d,g][1,3]dioxocin-6-carboxamide.

6. A compound of claim 2 which is 2,10-dichloro-N,N-dimethyl-12H-dibenzo[d,g][1,3]dioxocin-6-carboxamide.

7. A compound of claim 2 which is 1-(2,10-dichloro-12H-dibenzo-[d,g][1,3]dioxocin-6-carbonyl)piperidine.

8. A compound of claim 2 which is 4-(2,10-dichloro-12H-dibenzo-[d,g][1,3]dioxocin-6-carbonyl)morpholine.

9. A compound of claim 2 which is 2,10-dichloro-N(o-tolyl)-12H-dibenzo[d,g][1,3]dioxocin-6-carboxamide.

* * * * *

UNITED STATES PATENT OFFICE
CERTIFICATE OF CORRECTION

PATENT NO. : 3,931,173
DATED : January 6, 1976
INVENTOR(S) : Roger A. Parker and David L. Wenstrup It is certified that error appears in the above-identified patent and that said Letters Patent are hereby corrected as shown below:

Column 3, line 32 of the patent and page 4, line 12 of the specification, "phophoric" should read "phosphoric".
Column 4, lines 3, 4 and 7 of the table should read "6$\epsilon$, 0$\epsilon$, and 10$\epsilon$" and in the footnotes of the table should read "z = <0.1;"; line 3 of the patent and page 5, line 26 of the specification, "Tarryton" should read "Tarrytown".
Column 5, line 45, "225°-226°C." should read "225-227°C.".
Column 8, claim 4, line 1, "dichloro-12-dibenzo" should read "dichloro-12H-dibenzo".

Signed and Sealed this

Tenth Day of August 1976

[SEAL]

Attest:

RUTH C. MASON
*Attesting Officer*

C. MARSHALL DANN
*Commissioner of Patents and Trademarks*

UNITED STATES PATENT OFFICE
CERTIFICATE OF CORRECTION

PATENT NO. : 3,931,173
DATED : January 6, 1976
INVENTOR(S) : Roger A. Parker and David L. Wenstrup It is certified that error appears in the above-identified patent and that said Letters Patent are hereby corrected as shown below:

Claim 4, Column 8, of the patent reads "............. which is 2,10-dichloro-12-pyridylmethyl)-d,g][1,3]dioxocin-6-carboxamide" and should read "..........which is 2,10-dichloro-12H-dibenzo[d,g][1,3]dioxocin-6-carboxamide"

Signed and Sealed this

Twelfth Day of October 1976

[SEAL]

Attest:

RUTH C. MASON
Attesting Officer

C. MARSHALL DANN
Commissioner of Patents and Trademarks